US00PP28783P2

(12) United States Plant Patent
Pavlich

(10) Patent No.: US PP28,783 P2
(45) Date of Patent: Dec. 19, 2017

(54) ***BEGONIA* PLANT NAMED 'TNBEGRM'**

(50) Latin Name: ***Begonia* hybrid**
Varietal Denomination: TNBEGRM

(71) Applicant: Terra Nova Nurseries, Inc., Canby, OR (US)

(72) Inventor: John C. Pavlich, Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 14/999,824

(22) Filed: Jul. 5, 2016

(51) Int. Cl.
*A01H 5/02* (2006.01)

(52) U.S. Cl.
USPC ..... Plt./343

(58) Field of Classification Search
USPC ..... Plt./343
CPC ..... A01H 5/0238; A01H 5/02; A01H 5/00
See application file for complete search history.

(56) References Cited

PUBLICATIONS

Nursery Management Terra Nova Nurseries displays new varieties at 2016 California Spring Trials Apr. 8, 2016, retrieved on Aug. 10, 2016 , retrieved from the Internet at http://www.nurserymag.com/article/terra-nova-2016-trials/ 3 pp.*
Terra Nova Nurseries *Begonia* Revelation Maroon retrieved on Aug. 10, 2017, retrieved from the Internet at http://www.terranovanurseries.com/growers/begoniarevelationmaroon-p-819.html 2 pp.*

* cited by examiner

*Primary Examiner* — June Hwu
(74) *Attorney, Agent, or Firm* — Klarquist Sparkman, LLP

(57) ABSTRACT

A new and distinct form of *Begonia* plant characterized leaves colored burgundy to silvered burgundy with olive green along veins, dark burgundy red leaf backs, medium pink flowers, a trailing habit, and excellent vigor.

1 Drawing Sheet

Botanical denomination: *Begonia* hybrid.
Variety designation: 'TNBEGRM'.
Parentage: *Begonia hemsleyana* hybrid unnamed×*Begonia boliviensis* hybrid unnamed.

BACKGROUND OF THE INVENTION

The present invention relates to a new and distinct cultivar of *Begonia*, of the family Begoniaceae, and given the cultivar name, 'TNBEGRM'. This plant originated from a test cross with an unnamed *Begonia boliviensis* hybrid as the pollen parent. The new cultivar originated from a cross between *Begonia hemsleyana* unnamed hybrid (unpatented), as the seed parent and *Begonia boliviensis* hybrid unnamed (unpatented), as the pollen parent. There are no similar *Begonia* on the market known to the inventor. This selection is uniquely characterized by:

1. leaves colored burgundy to silvered burgundy with olive green along veins,
2. dark burgundy red leaf backs,
3. medium pink flowers,
4. a trailing habit, and
5. excellent vigor.

Compared to the seed parent *Begonia hemsleyana* hybrid unnamed, an unpatented plant, the new cultivar has leaves a trailing rather than an upright, shrubby habit and dark simple leaves rather than green to silver palmately compound.

Compared to the pollen parent, *Begonia boliviensis* hybrid unnamed, an unpatented plant, the new cultivar is trailing rather than sprawling, with smaller flowers that are pink rather than red orange, and maroon leaves instead of green.

The new variety has been reproduced only by asexual propagation (leaf cuttings and tissue culture). Each of the progeny exhibits identical characteristics to the original plant. Asexual propagation by micropropagation using the meristem as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 9-month old in a growing in a 10 inch hanging basket in a warm greenhouse in March in Canby, Oreg.

FIG. 2 shows a one-year old plant of the new cultivar growing in early summer in bloom in a warm greenhouse in Canby, Oreg.

FIG. 3 shows a close up of a flower and leaves of the same plant.

DETAILED PLANT DESCRIPTION

The following is a detailed description of the new *Begonia* cultivar based on observations of 9-month-old specimens grown in one gallon containers in a warm greenhouse in June in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on *The Royal Horticultural Society Colour Chart,* 5th edition, 2007.

Plant:

*Type*.—Tropical perennial.

*Form*.—Trailing.

*Cold hardiness*.—USDA Zone 10.

*Size*.—Trailing to 60 cm and 43 cm wide.

*Vigor*.—Excellent.

*Roots and rooting*.—Roots appear on leaf cuttings in 2 weeks; fine, fibrous, and white in color.

Stem:

*Type*.—Decumbent.

*Size*.—Grows to 44 cm long and 6 mm wide.

*Internodes*.—From 1 cm to 2.5 cm long.

*Surface*.—Pubescent.

*Lateral branches*.—Where pinched.

*Color*.—Greyed Brown N199A.

Leaf:

*Type*.—Simple.

*Arrangement*.—Alternate.

*Number per stem*.—About 20.

*Leaf strength*.—Excellent, tough, leathery.

*Blade size*.—Grows to 7 cm wide and 12 cm long.

*Shape*.—Ovate.

*Margins*.—Very shallowly 4 to 5 lobed, dentate to denticulate.

*Apex*.—Acuminate.

*Base*.—Oblique and cordate.

*Venation*.—Palmate, topside Green 138B, bottom side Greyed Purple 187A.

*Surface texture*.—Pubescent on both sides.

*Stipules*.—Deciduous, ovate, 10 mm long and 5 mm wide, apex aristate, base sessile and clasping ,entire, back side pubescent, inside glabrous, both sides Greyed Red 181B.

*Petiole description*.—2.5 cm to 6.5 cm long and 2.5 mm wide, succulent, pubescent, Greyed Brown N199A on topside and Greyed Purple 187B on bottom side.

*Leaf color*.—Topside in low light Greyed Purple 187C with the 2 mm on either side of the veins closest to Green N138B, bottom side Greyed Purple 187A; topside in high light there is an overlay of N187B over Greyed Purple 187C with the 2 mm on either side of the veins closest to Green N138B, bottom side Greyed Purple 187A.

Inflorescence:

*Type*.—Axillary, bisexual (only tepals, no pistil or stamen), cymose.

*Number of flowers per cyme*.—Usually 4 to 5.

*Peduncle description*.—Grows 39 mm long and 1.5 mm wide, glabrous, fleshy, of good strength , Greyed Orange 176A; with 2 opposite, dehiscent petiolate leaf-bracts below each cyme, deciduous, ovate-lanceolate, 13 mm long and 10 mm wide, apex mucronate, margin ciliate, both sides glabrous and Yellow Green 147C.

*Pedicel description*.—Grow to 15 mm long, 1 mm wide, fleshy, glabrous, of good strength, Red Purple 68D.

*Bloom period*.—Late winter to mid-summer in Canby, Oreg.

Flower bud:

*Size*.—11 mm long and 11 mm wide prior to opening.

*Shape*.—Flattened teardrop.

*Surface texture*.—Glabrous.

*Color*.—Red Purple 68A with edges 68C.

Flower:

*Type*.—Male and female sterile, no pistil or stamen, bilaterally symmetrical.

*Flower*.—Grows to 15 mm deep and 35 mm wide overall; 4 fleshy tepals, topside Red Purple 68C, bottom side 68C; outer 2 tepals ovate, entire, tip obtuse, base truncate; two inner tepals broadly obovate, margin undulate, tip retuse, base attenuate.

*Fragrance*.—None.

*Lastingness*.—A cyme blooms for about 4 weeks on the plant; flowers are self-cleaning.

Fruit and seed: None, sterile.

Diseases and pests: The new cultivar is typical to the genus. No known resistances to pests or diseases. No problems have been found in Canby, Oreg.

I claim:

1. A new and distinct form of *Begonia* plant as hereby illustrated and described.

* * * * *

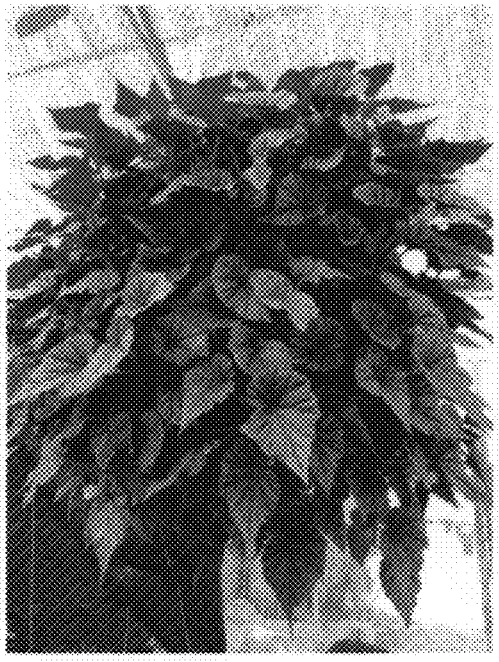
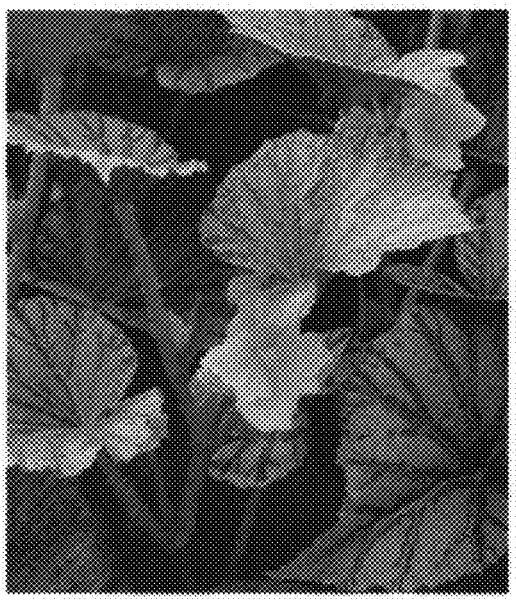

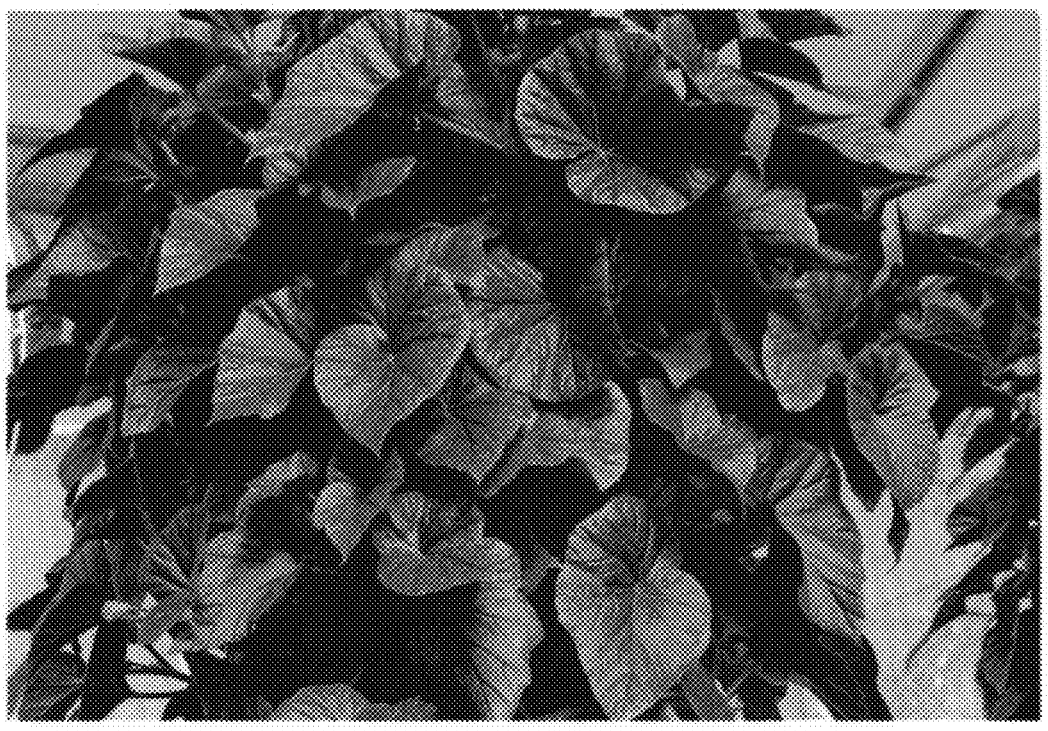
FIG. 1 above, FIG. 2 below left, FIG. 3 below right